US010064975B2

(12) United States Patent
Hiraiwa

(10) Patent No.: US 10,064,975 B2
(45) Date of Patent: Sep. 4, 2018

(54) METHOD FOR COATING SKIN ABRASION, LACERATION, BURN OR OEDEMA AFTER SURGERY

(71) Applicant: Lilac Laboratory Co., Ltd., Saitama-ken (JP)

(72) Inventor: Ryoichi Hiraiwa, Saitama-ken (JP)

(73) Assignee: Lilac Laboratory Co., Ltd., Saitama-ken (JP)

( * ) Notice: Subject to any disclaimer, the term of this patent is extended or adjusted under 35 U.S.C. 154(b) by 0 days.

(21) Appl. No.: 14/931,860

(22) Filed: Nov. 4, 2015

(65) Prior Publication Data
US 2016/0136324 A1 May 19, 2016

(30) Foreign Application Priority Data

Nov. 17, 2014 (JP) ................................ 2014-246275

(51) Int. Cl.
*A61L 26/00* (2006.01)
(52) U.S. Cl.
CPC ....... *A61L 26/0004* (2013.01); *A61L 26/0023* (2013.01); *A61L 26/0085* (2013.01)
(58) Field of Classification Search
CPC ............. A61L 26/0004; A61L 26/0085; A61L 26/0023
USPC ........................................................ 424/685
See application file for complete search history.

(56) References Cited

U.S. PATENT DOCUMENTS

| 2002/0119109 A1 | 8/2002 | Herpens et al. | |
| 2004/0136941 A1* | 7/2004 | Max | A61K 8/26 424/70.13 |
| 2007/0031515 A1* | 2/2007 | Stucky | A61K 33/24 424/724 |
| 2007/0264315 A1 | 11/2007 | Fournie et al. | |
| 2008/0254094 A1 | 10/2008 | Martel et al. | |
| 2014/0348921 A1 | 11/2014 | Lesage | |

FOREIGN PATENT DOCUMENTS

| DE | 10123989 A | 11/2002 |
| JP | H07-33647 A | 2/1995 |
| JP | 2002-60320 A | 2/2002 |
| JP | 2009-536184 A | 10/2009 |
| JP | 2012-111732 A | 6/2012 |
| JP | 2014-529339 A | 11/2014 |
| WO | WO 2002009782 A1 * | 2/2002 |

OTHER PUBLICATIONS

Henley et al.; title: Hemostatic agents used in the practice of dermatologic surgery, Dermatology Research and Practice, vol. 2013 (Article ID 279289), pp. 1-15, published Jul. 7, 2013.*
Schneider et al, title: Influence of pH on wound-healing: a new perspective for wound-therapy? Arch Dermatol Res, vol. 298, pp. 413-420; published online Nov. 8, 2006.*
Japanese notice of the reason for refusal dated Mar. 24, 2015.
Japanese decision to grant a patent dated Jul. 7, 2015.
Local hemostasis agent in oral cavity, Dental use TD Zett Jelly, Sep. 2009, https://www.bee.co.jp/pdf/siryou/12a.pdf.
German Office Action dated May 30, 2016.
Firla M. T., Efficient tissue management with Raccegel, case study Jun. 2012, pp. 4-9.
Sven Schomaker, empiric comparison study confirms thixotropic wound dressing for hemostasis, DT today News, 7+8 2014, p. 28.
Mehr zum Thema, products Racegel for preparing the gingiva, ZM—dentists' communications, Aug. 28, 2012.

* cited by examiner

*Primary Examiner* — Yanzhi Zhang
(74) *Attorney, Agent, or Firm* — Yokoi & Co., U.S.A.; Toshiyuki Yokoi

(57) ABSTRACT

The present invention relates to a biological film-forming agent which is for facilitating wound healing and coating and protecting biological organs, and for coating and protecting damaged cells, wound surfaces, organs and damaged sites of organs, and wound surfaces reaching soft tissues such as muscle and facia, periosteum or bone cortex. Provided is a biological film-forming agent for suppressing exudation of intracellular fluid from damaged cells, suppressing expansion of inflammation reactions and secondary inflammation reactions resulting from production of fibrin and eliminating adverse effects caused by formation of stabilised fibrin on healing. Various problems can be solved by using the agent containing aluminium chloride, cyclodextrin and water as base components.

9 Claims, 11 Drawing Sheets

METHOD FOR COATING SKIN ABRASION, LACERATION, BURN OR OEDEMA AFTER SURGERY

CROSS-REFERENCES TO RELATED APPLICATIONS

This patent specification is based on Japanese patent application, No. 2014-246275 filed on Nov. 17, 2014 in the Japan Patent Office, the entire contents of which are incorporated by reference herein.

BACKGROUND OF THE INVENTION

1. Field of the Invention

The present invention relates to a dressing which can form an extremely thin porous film having both water repellency and defatting property over wound surfaces and damaged cells to coat the wound surfaces and damaged cells in order to prevent exudation of intracellular fluid from the damaged cells, thereby suppressing inflammation reactions, alleviating spontaneous pain and facilitating wound healing. The present invention relates to a biological film-forming agent which serves as a cell-contacting coating and protecting agent of internal and external surfaces of various organs, for coating and protection of wound surfaces, various organs and damaged sites of various organs as well as wound surfaces reaching soft tissues such as muscle and fascia; periosteum and bone cortex in order to suppress intestinal oedema accompanying inflammation reaction at suture sites or due to vascular anastomosis and open surgery and prevent development of adhesive ileus and the like.

2. Description of Related Art

There are known dressings of wound surfaces such as gauze, bandages, Sofra-Tulle adhesive patch, polyurethane films of spray agents, silicone gauze, trafermin preparations, cultured epidermis, bone marrow stem cells for regenerative therapy and IPS cells. However, use of conventional products which merely coat wound surfaces do not suppress continuous exudation of intracellular fluid from damaged cells, and thus acute inflammation reactions occur not only at wound surfaces but also at skin surrounding the wounds, resulting in associated strong pain and a high amount of inflammatory exudate. Continuous exudation creates a condition prone to bacterial infection and as a result frequent exchange of dressings and more than one symptomatic treatment such as disinfectants, antibiotic ointments, powders and anti-inflammatory topical agents is required in order to prevent secondary bacterial infections and inflammation reactions.

In practical medical use, the use of any conventional dressings is associated with adverse effects of adhesion of wound surfaces due to inflammatory exudate and stabilised fibrin in the exudate serving as a biological adhesive component and thus bleeding due to detachment of the wound surfaces every time the dressings are exchanged. This may result in not only another tissue damage but also continuous inflammation reactions, in addition to wound surfaces, at the edges and surroundings of the wounds and is a major cause of induction of strong pigmentations, hyperplasia of collagen fibre and thus scars and agglomeration after healing, and development of hypertrophic scars and keloids depending on the area of the body and body constitution.

BRIEF SUMMARY OF THE INVENTION

An object of the present invention is to decrease fat, which is harmful for wound healing, and to suppress production of fibrin and exudation of intracellular fluid by forming, unlike conventional therapeutic agents, an extremely thin, water repellent and defatting film which has tissue affinity towards damaged surfaces and damages cells. As a result, inflammation reactions can be suppressed, pain can be alleviated, the amount of exudate can be reduced and secondary bacterial inflammation can be prevented. Thus cleaning of contaminated wounds or complicated wound treatment may be omitted, complex wound surfaces may be kept dry only by application, secondary tissue damage and pain due to stabilised fibrin and adhesion of wound surfaces resulting from use of conventional dressings such as gauze can be prevented and an optimal environment and a preferable condition for wound healing can be provided, and thus early healing can be provided and various adverse effects after healing such as pigmentations can be remarkably eliminated.

The water repellent and porous film means a film which does not inhibit transpiration of water in the body (e.g. sweat) through a space of the film although the film has a property of repelling water. It is considered that the function of transpiration of water, the defatting function and the function of blocking protein are greatly related with each other. Here, the function of blocking protein is achieved by the combination of the agent of the present invention and the protein. When the above described functions are combined, the function of suppressing production of fibrin is considered to be generated.

As a result of study on interaction of aluminium chloride, cyclodextrin and water and physiochemical effects of the combination of these materials, it was found that an interfacial surface having strong water repellent and hydrophobic property was formed and the emulsion formed by skin stratum corneum, sweat and sebum was demulsified by that. Further, defatting property is improved because encapsulation of fat such as sebum is urged by the cyclodextrin. Further, defatting property is urged because the formed film is porous and thus does not inhibit water transpiration from the body. Further, the film reduces friction and thus friction between various organs and external friction can be reduced (sliding effect). The present invention is a result of application of these properties.

FIG. 1 is a photographic image showing a state of applying the agent of the present invention containing aluminium chloride hydrate on the skin to coat the surface of skin and the whole stratum corneum, which repels water, as one of the examples of water repellent action.

It was found that aluminium chloride, cyclodextrin and water interact to prevent exudation of intracellular hydrophilic components such as proteins, amino acids and glucose from damaged cells on wound surfaces or damaged vessels and encapsulate or absorb lipophilic components including emulsions, thereby providing an extremely optimal environment and preferable conditions for wound healing. As for the various components exuded from damaged cells and damaged vessels include lipophilic components, the water-repellent, defatting and vapor water permeable film formed with aluminium chloride, cyclodextrin and water prevents exudation of intracellular fluid from damaged cells, resulting in suppression of production of fibrin and alleviation of inflammation reactions according to a number of case results on wound surfaces, damaged cells and damaged vessels. When applied to dermal wound sites, effects can be obtained in that oedema and pain are significantly alleviated and the amount of exudate is remarkably reduced even in widespread skin damage such as burns or deep wounds reaching subcutaneous fat.

As a result of suppression of stabilised fibrin production, improved detachment of gauze or conventional dressings results and another wound is not induced, and thus exudation at wound surfaces in conventional wound healing and exudation of intracellular fluid are significantly suppressed. Further, skin pigmentation after inflammation, hypertrophic scars and keloids occurring due to continuous expansion of inflammation reactions can be significantly prevented.

The present invention does not aim at haemostasis, and is an invention which rather facilitates an action opposite to the haemostasis. When applied on wound surfaces, although mechanism of action is unknown, the present invention can immediately arrest petechial haemorrhage (haemorrhage due to breakage of capillary vessels up to the dermal papilla lower layer) and can arrest effusive haemorrhage (haemorrhage due to breakage at the level of venule in the mid-upper dermis) within 2 minutes which is shorter than the time required with platelets.

Furthermore, it was also found that a water-repellent defatting film is formed on the target surface of various organs represented by a wound surface, friction is reduced and lubricity is increased, and therefore the present invention can provide a useful effect to intestinal adhesive ileus accompanying inflammatory intestinal oedema upon open surgery.

It was also found that a water-repellent defatting film is formed and fixed on the surface of damaged cells deteriorating over time from excised organs upon organ transplant, for example, thereby inhibiting exudation of intracellular fluid and exhibiting an organ protection effect.

In order to form a biological film-forming agent, water is an essential conditions. An example of formulation is, relative to 100 g of water, in weight ratio, 0.1 to 25% of aluminium chloride and 0.1 to 45% of cyclodextrin. Aluminium chloride may be anhydride or hydrate, and although the effect is less, aluminium hydroxychloride, alum or a polymer of basic aluminium chloride may be used.

In order to use at a wound site containing excess water (body fluid) such as leaking blood or exudate, a dosage form of powder may be preferable because while absorbing excess exudate, a simulated crust containing fine powder may be formed and a film may be more effectively formed at a complex boundary to the wound site. Fine powder is produced by appropriately adding main agents of the present invention, aluminium chloride powder and cyclodextrin powder, to the powder of base auxiliary agents which are advantageous in powderisation. The main purpose of use of the powderisation base auxiliary agent is to reduce powder blocking due to the hygroscopic and deliquescent nature of the aluminium chloride compound and to improve pulverisation property as well as to improve flowability and dispersibility of a powder agent. Examples of the powderisation base auxiliary agent include silicic anhydride, *Trichosanthes kirilowii*, starch such as corn starch and phosphoric acid-modified starch and other powder agents such as zinc oxide and talc.

Cyclodextrin (hereinafter abbreviated as CD) used in the present invention can, thanks to the interaction with water and aluminium chloride, demulsify and absorb hydrophobic substances such as sebum or emulsion of sebum and water in sweat. In the present invention, cyclodextrin mainly refers to α-CD, β-CD, γ-CD and mixture thereof and may include derivatives thereof.

Since the defatting property and the function of blocking protein is urged and the production of fibrin is suppressed, inflammation reaction and immunoreaction are suppressed and the possibility of application to and improvement in the following symptoms and diseases is facilitated by the effect of an increase in lubrication:

(1) use for reduction of inflammation reactions and pain relief after aphthous stomatitis and tooth extraction, and anti-inflammation of dental leakage;
(2) use for stably securing an effect of surgery, reduction in hospitalisation period and facilitation of rehabilitation by coating and protection of organs after surgery and reduction in inflammation reactions in the field of cerebral, spinal and neurosurgery;
(3) use for reduction in thrombus, omission and rejection due to immunoreaction (inflammation reaction) in transplanted vessels by microsurgery and capillary anastomosis and avoidance of skin flap necrosis in the field of plastic surgery, reconstructive surgery and organ transplant action;
(4) upon microsurgery in the field of plastic surgery, prevent thrombus in grafted vessels, protect grafts and vessels, suppress vascular oedema and improve the graft rate;
(5) use for suppression and symptom relief of bronchial stenosis accompanying irritating sensations by foreign matters in airway epithelium in asthma patients and COPD (chronic respiratory distress syndrome) patients (bronchoscopic use);
(6) use for significant suppression of systemic pain in severe burns, reduction in inflammation reactions, early wound healing without relying on skin grafting or cultured epidermis, prevention of secondary bacterial infection, reduction in admission period, facilitation of rehabilitation and reduction in ugliness;
(7) use for pain relief of gastroduodenal ulcer (endoscopic use) and reduction in inflammation reactions;
(8) use for pain relief and anti-inflammation of anal fissure by intra-anal canal use and promotion of anti-inflammation effect by combined use with petrolatum or a lubricant;
(9) use for suppression of irritating sensation of foreign substances in intranasal administration and reduction in nasal discharge and nasal obstruction by reduction in inflammation reactions in allergic rhinitis;
(10) use for protection of tympanic membrane after drainage, protection of ear ossicle and anti-inflammation in otitis media;
(11) use for alleviation of inflammation reactions after probing by lacrimal duct bougie, coating and protection of damaged epithelium of nasolacrimal duct in inflammatory blockage of nasolacrimal duct;
(12) wound control of skin abrasion and laceration, incision wound and tear reaching skin and subcutaneous tissues, facia, muscle, cartilage, periosteum or bone, facilitation of crust formation and epidermalisation, reduction in healing period of trauma and surgical wound and effacement of skin traumatic pigmentation and scars;
(13) reduction in acute inflammation reactions (swelling, oedema, pain), suppression of persistent inflammation reactions, prevention of necrosis of muscle and bone tissues and sequestration due to secondary infection, and avoidance of leg amputation as a last resort in open fracture;
(14) prevention of scar contracture, avoidance of functional impairment and conduct disorder such as flexion contracture and extension limitation and avoidance of skin dysmorphogenesis by avoiding and supressing inflammation reactions by three-dimensional coating of damaged cells to suppress activities of fibroblast and suppressing hyperplasia of collagen fibres to lead to the earliest and appropriate wound healing process in burns of flexor aspects of fingers and toes and neck of mandible;

(15) as a local therapy of cancer, to be mixed with an anti-cancer drug and apply or spray to a main focus of cancer or a metastatic cancer site to coat the focus of cancer and prevent disseminated metastasis and achieve reduction of cancer. It can be conveniently used for cancer cells as well as various organ tissues in vivo and does not cause any adverse effect even when it remains, and thus it can be an alternative means that can effectively and inexpensively carry out the conventional cancer therapy;

(16) to prevent anastomotic leakage in gastrointestinal, hepatobiliary, respiratory and gynaecological surgeries. To reduce the period until the inflammatory oedema appears after surgery, reduce admission period and facilitate rehabilitation; and

(17) to be infiltrated to tissues regenerated with IPS cells, cultured epidermis, cornea or the like and increase the graft rate to affected sites.

DETAILED DESCRIPTION OF THE INVENTION

Figure 1:
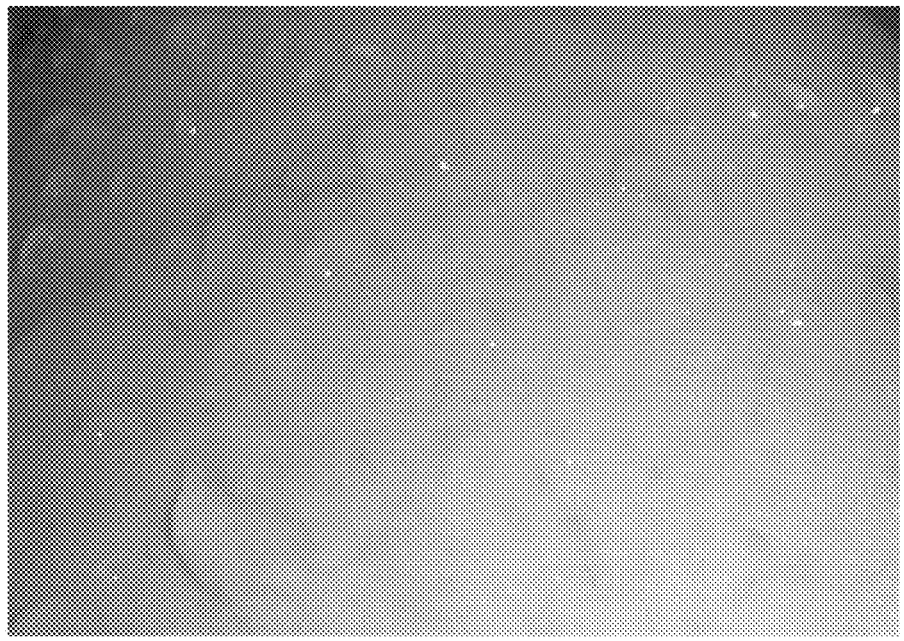
FIG. 1 is a photographic image of a thin aluminium chloride film coating a skin surface or a whole stratum corneum while repelling water.

According to the present invention, an active ingredient, aluminium chloride hydrate, is preferably used at the practical range of 0.005% to 20% by weight in view of the strong acidity thereof and tissue irritating nature. The pH of aluminium chloride is less affected by the concentration and is as low as around pH 1.9. Aluminium chloride has strong tissue irritating nature, and thus is more preferably adjusted to pH of 2.8 to 6.0 in practical use.

A base component, water, may be purified water or pure water or, depending on the application condition (mucosa, conjunctiva), physiological saline such as an isotonic solution containing sodium chloride as a main component may be preferable. If the dosage form is powder, water content in body fluid such as sweat, nasal discharge, lacrimal fluid, saliva, tracheal and bronchial secreta, blood, inflammatory exudate, gastric mucus and gastric juice, small intestinal mucus, pleural fluid, ascitic fluid, water that moistens the surface of retroperitoneal organs, water that moistens cardiac and great vessels in mediastinum, cervical discharge, vaginal discharge, and anal gland discharge can be used as the water of main component. When causing an irritating feeling and increased pain, pH can be raised to at least 2.8 by disacidifying the agent with an alkaline agent such as sodium hydroxide and adding flocculation agent such as xanthan gum, guar gum, soluble starch and polyacrylic acid to filter the generated flocculated precipitates containing aluminum chloride and aluminum hydroxide. Thus, tingling sensation is reduced and safe usage is allowed without causing acidic histological damage in all organs in the body.

If the dosage form is powder, pH can be raised to at least 2.8 by arbitrarily adding alkaline powders such as silica, sodium carbonate and potassium hydroxide. Thus, tingling sensation is reduced and safe usage is allowed without causing acidic histological damage in all organs in the body.

Cyclodextrin that can be used for the present invention may be α-, β- or γ-cyclodextrin or a mixture thereof. Preferably, hydroxyalkylated β-cyclodextrin is economically advantageous. Examples for α-cyclodextrin and γ-cyclodextrin are omitted; however α-cyclodextrin and γ-cyclodextrin did not show any significant difference in the function effect from β-cyclodextrin.

Dosage forms which can be used for the present invention are lotions, powder, sprays, ointments, creams, tinctures and the like. However, when using the agent to wash the wound, the agent can be included in detergents such as surfactant. An advantage of the dosage forms is that a sufficient amount can be applied to obtain permeation through wound surfaces and surrounding skin.

Optionally, drugs such as antibiotics, a humectant such as propylene glycol and glycerol, an ordinary viscosity adjusting agent such as gelatine, hydroxymethylcellulose and hydroxyethylcellulose may be arbitrarily added to provide viscosity.

Preferable Examples are hereinafter described in detail.

EXAMPLE 1

To 500 ml of purified water, base components 1 and 2 were dissolved followed by the addition of 3, 4, 5 and 6 and the mixture was stirred.

| 1. Aluminium chloride hexahydrate | 45.50 g |
| 2. β-Cyclodextrin | 6.50 g |
| 3. Xanthan gum | 1.50 g |
| 4. Glycerol | 20.0 g |
| 5. Propylene glycol | 20.0 g |
| 6. 10% sodium hydroxide solution | 15.0 g |
| 7. 70% ethanol preparation | 9.0 g |

In the present Example, in order to reduce irritating nature at affected areas due to the acidity of aluminium chloride, 3.0% of the 10% sodium hydroxide solution was added to neutralise, the produced precipitate was removed by filtration and pH was adjusted to 3.9. The resulting solution did not have any action as a bactericidal agent and had fungus growth after a 1-week storage at a normal temperature to form colonies like spherical moss. Therefore, the 70% ethanol preparation was added as a fungicide.

<Case 1 of Example 1>

Use example to knee abrasion: An abrasion with the maximum size of 15 mm×15 mm in a 10-year-old boy. The boy had repeatedly fallen to scratch the same site over 3 years, and thus the outside of the wound surface showed the formation of an elevated hypertrophic scar.

Figure 2:
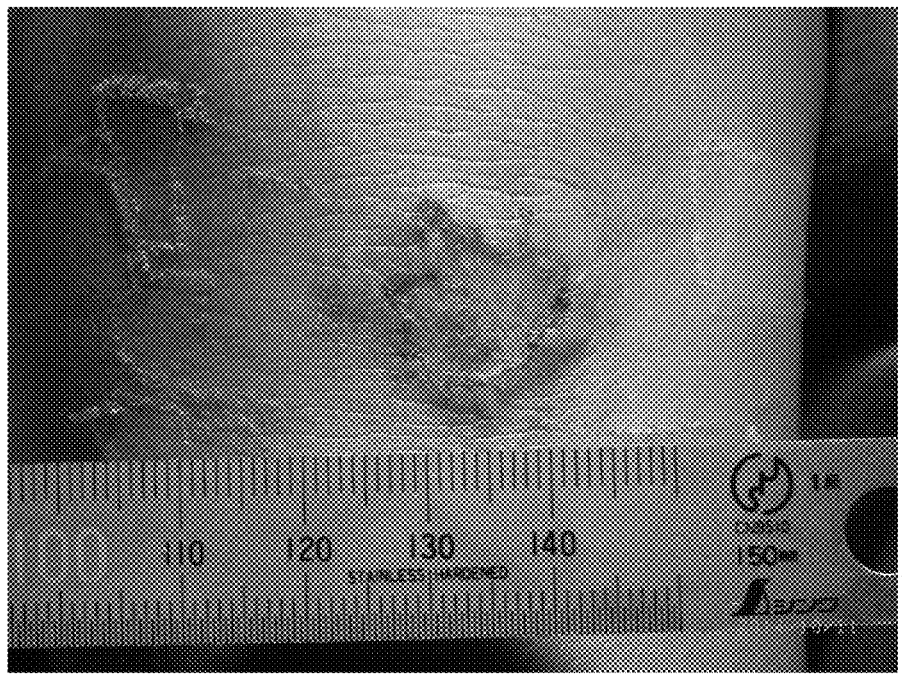
FIG. 2 is an observation of formation of a water-repellent defatting film which exhibiting haemostatic action immediately after directly applying an aqueous solution according to Example 1 of the present invention without disinfection.
Figure 3:
FIG. 3 is a photographic image showing that a scar is not elevated, has already lost redness or stiffness and is getting matured.

FIG. 2 is an observation of formation of a water-repellent defatting film which exhibiting haemostasis action immediately after directly applying an aqueous solution according to Example 1 of the present invention without disinfection. Formation of a film immediately after applying Example 1 after the injury and visit: With the consent of mother of the patient, the patient received 10 mL of Example 1 and applied Example 1 once daily after taking a bath with exchange of gauze. The patient made another visit after 33 days (FIG. 3). As shown in FIG. 3, although it was a secondary site of a hypertrophic scar with repetitive bending and stretching, the scar was not elevated, already lost redness or stiffness and was getting matured. Pigmentation after inflammation did not occur.

<Case 2 of Example 1>

Figure 4:
FIG. 4 is a case of a dorsum of a right hand affected by a 2nd degree burn (superficial) due to contact with a lid of a pan.
Figure 5:
FIG. 5 is a photographic image showing the status one week after FIG. 4.

Use example to a dorsum of a right hand with a 2nd degree burn: A 55-year-old woman who touched a lid of a pan to be affected on a dorsum of her right hand by a 2nd degree burn (superficial) (FIG. 4). The patient applied Example 1 once daily with exchange of gauze. The patient made another visit after one week (FIG. 5). Formation of epidermis was completed at a site with blister formation and almost no pigmentation after inflammation was observed. Generally, completion of epidermalisation in a 2nd degree burn requires 14 days or more, a blister tends to be ruptured, blister roof tends to be adhered to gauze during exchange of gauze, erosion may occur, healing may be protracted and a hypertrophic scar may occur; however, in this case, a clean epidermalisation was observed after 7 days of injury (FIG. 5). At the time of injury (at the first visit) (FIG. 4) and at a second visit (7 days after injury) (FIG. 5).

<Case 3 of Example 1>

Figure 6:
FIG. 6 is a photographic image showing haemostatic action of Example 1 (case study 3) on effusive haemorrhage observed after removal of molluscum contagiosum.

Use example to demonstrate haemostatic action on an effusive haemorrhage observed after removal of molluscum contagiosum: A 6-year-old boy. Molluscum contagiosum was removed with a puncture device and Example 1 was applied immediately thereafter with cotton wool. Effusive haemorrhage from the affected site was arrested within 10 seconds. (FIG. 6) haemostatic action by Example 1.

<Case 4 of Example 1>

Figure 7:
FIG. 7 is a photographic image showing 2nd degree burn accompanied by oedematous blister of 20 mm extending between thumb and index finger of right palm.

A 2-year-old girl. The patient touched an iron on 26 October and was affected by a 2nd degree burn on her right palm. After visiting a dermatologist and being prescribed with an antibiotic ointment and a disinfectant, the patient experienced an expanded blister and strong pain, and thus visited on 30 October the present inventor who is a dermatologist and plastic surgeon. At the first visit, the patient was diagnosed with a 2nd degree burn accompanied by a 20-mm oedematous blister extending between thumb and index finger of her right palm (FIG. 7). As shown in FIG. 7, when the area of blister formation of the 2nd degree burn (at the first visit) on right palm is small, the blister is tight and filled to cause strong pain, and thus the blister was immediately punctured and (Example 1) was applied. A non-steroidal anti-inflammatory ointment was then applied. From the experience of the inventor, an antibiotic ointment was unnecessary and thus was not used.

Figure 8:
FIG. 8 is a photographic image showing one week after FIG. 7 when epidermalisation is completed.

The parents of the patient were instructed to apply [Example 1] once daily in evening with fingers without regard to contamination, then apply a non-steroidal anti-inflammatory ointment, cover with gauze and fix with a mesh bandage. Another visit was made after 1 week (FIG. 8). At the second visit (after one week), the patient replied that she had no pain to the inquiry of the degree of pain. As shown in FIG. 8, epidermalisation was completed, blister roof was beginning to desquamate and no keloid or hypertrophic scar formation was observed.

The parents of the patient were instructed to apply only the formulation of [Example 1] until the original skin colour was restored. Paediatric 2nd degree burn where the epidermis is thinner than adults may become severe and, in case of the affected site as the present case, extension disorder of fingers may be observed due to hypertrophic scar or stiffening of scar. Therefore, it is important to suppress inflammation reactions and promote wound healing. As described above, the present invention allows early wound healing which could not be realised with the conventional art. The present invention can also be applied to severe burns with a wide area at any sites, allows pain relief and early healing and does not cause an ugly scar or disordered function. Thus the present invention is also excellent in ease of usage and value for money.

EXAMPLE 2

To 500 ml of saline, base components 1 and 2 were dissolved followed by the addition of 3, 4, 5 and 6 and the mixture was stirred.

| 1. Aluminium chloride hexahydrate | 60.0 g |
| 2. β-Cyclodextrin | 5.0 g |
| 3. Glycerol | 20.0 g |
| 4. Propylene glycol | 20.0 g |
| 5. 70% ethanol preparation | 9.0 g |

In the present Example, in order to reduce irritating nature at affected areas due to a low acidity of aluminium chloride of pH 1.9, components 3 and 4 were added as buffering agents. The aqueous solution containing base components had low bacteriostatic or bactericidal action and had fungus growth after a 1-week storage at a normal temperature to form colonies like spherical moss. Therefore, the 70% ethanol preparation of component 5 was added as a fungicide.

<Case 5 of Example 2>

Figure 9:
FIG. 9 is a photographic image showing initiation of epidermalisation with crust being lifted.
Figure 10:
FIG. 10 is a photographic image showing the status of the patient of FIG. 9 after 24 days.
Figure 11:
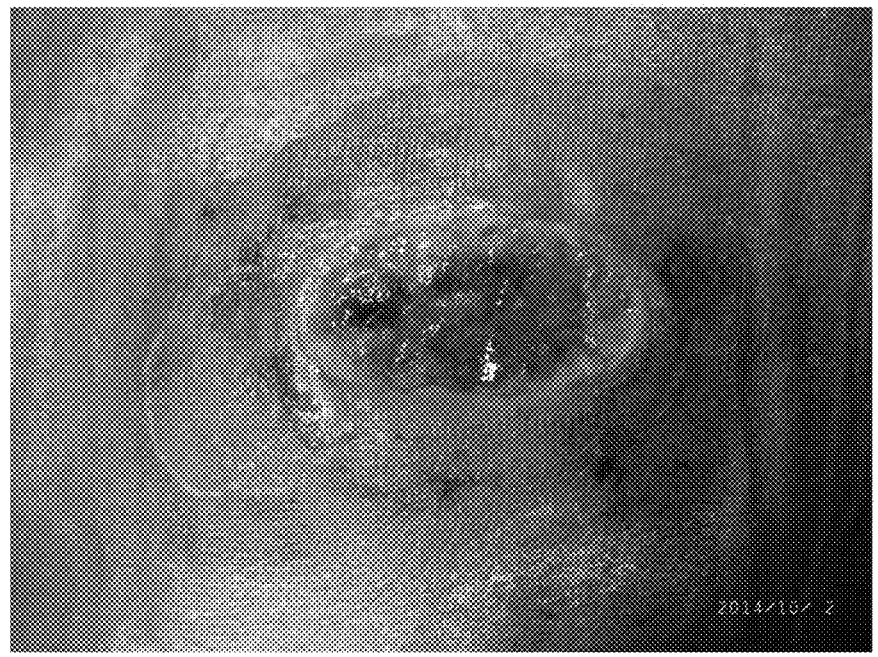
FIG. 11 is a photographic image showing the status 7 days after treatment with the formulation of Example 3.
Figure 12:
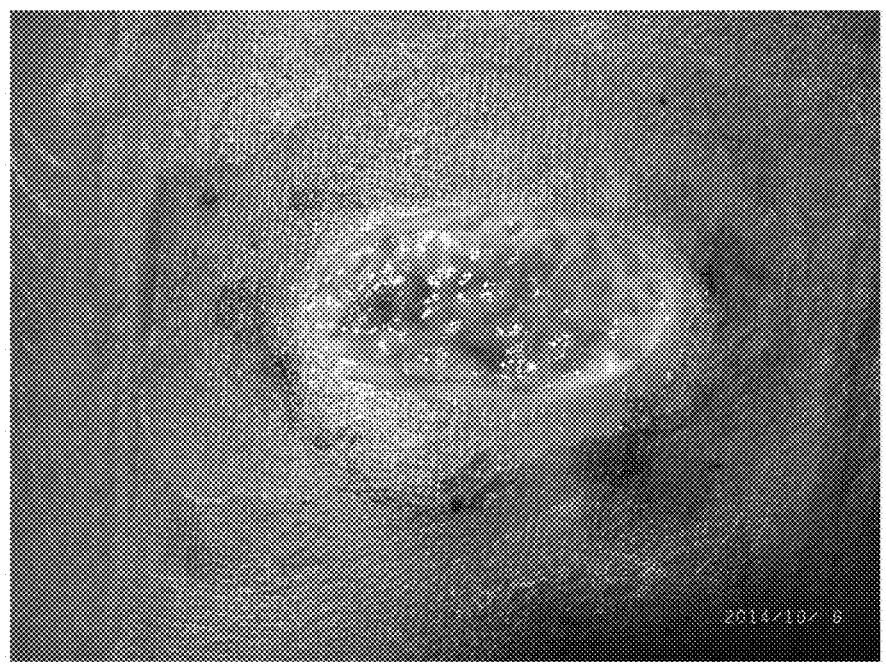
FIG. 12 is a photographic image showing the status 11 days after treatment with the formulation of Example 3.
Figure 13:
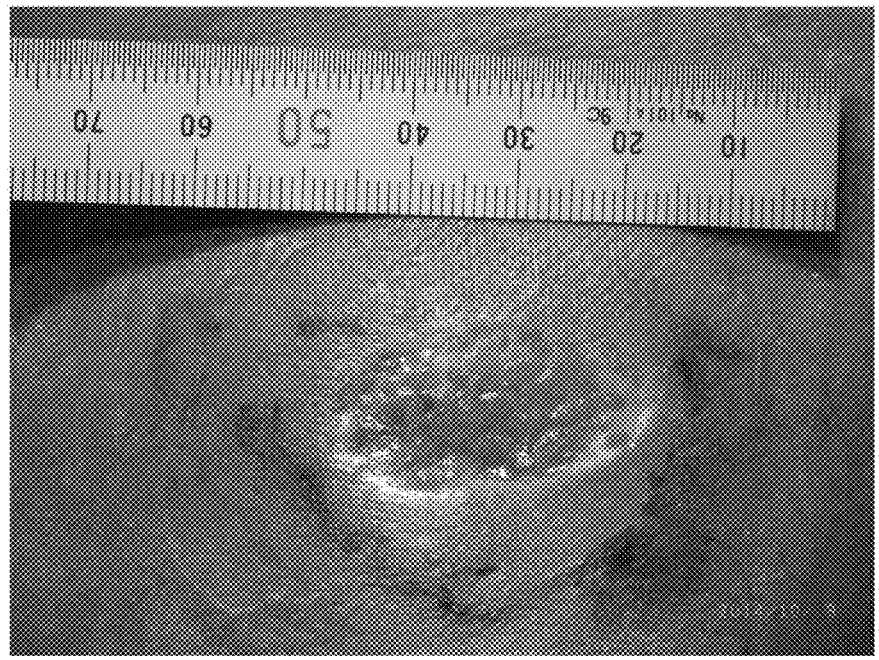
FIG. 13 is a photographic image showing the status 14 days after treatment with the formulation of Example 3.
Figure 14:
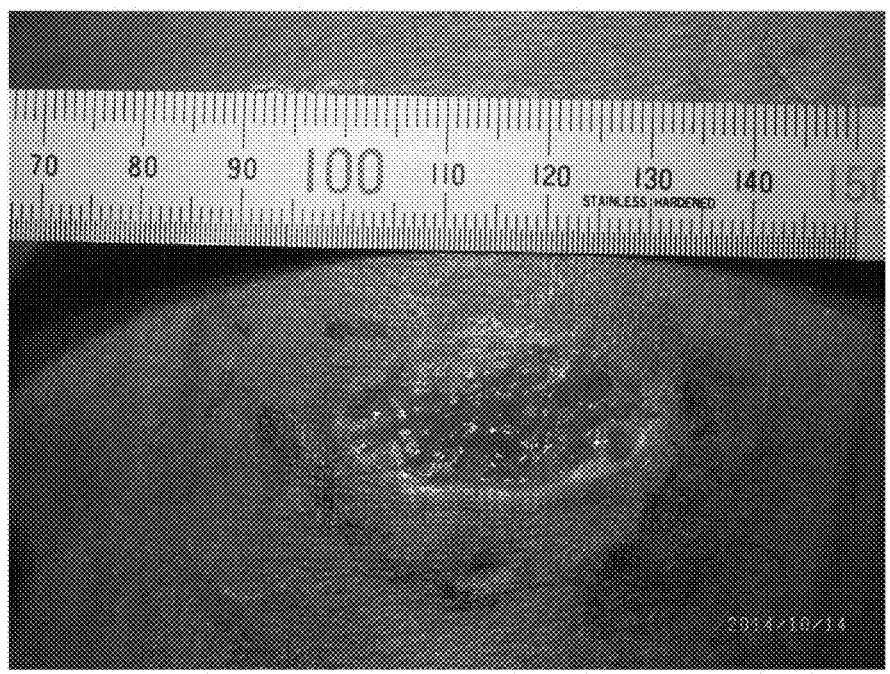
FIG. 14 is a photographic image showing the status 20 days after treatment with the formulation of Example 3.
Figure 15:
FIG. 15 is a photographic image showing the status 24 days after treatment with the formulation of Example 3.
Figure 16:
FIG. 16 is a photographic image showing the status 36 days after treatment with the formulation of Example 3.
Figure 17:
FIG. 17 is a photographic image showing the status 39 days after treatment with the formulation of Example 3.

An example of abrasion on left forearm. The patient hit on left forearm against a rock during mountain climbing to suffer abrasion. The depth of wound was up to mid-upper dermis. Immediately after the climbing, Example 2 was applied. At the moment of application, the patient experienced stinging pain due to the acidity of aluminium chloride hexahydrate, which was disappeared within 10 seconds from the affected site. Without using a conventional dressing, only Example 2 was continuously applied twice daily (morning and after taking a bath). After the visit, crust formation was already observed and after 4 days of injury, it was observed that crust was lifted and epidermalisation was initiated (FIG. 9). After 24 days of injury, the colour of skin was already matched to the surroundings without scar and no pigmentation after inflammation at the edges of scar was observed (FIG. 10). FIG. 9 is 4 days after injury and FIG. 10 is 24 days after injury.

EXAMPLE 3

To 500 ml of purified water, base components 1 and 2 were dissolved followed by the addition of 3, 4, 5 and 6 and the mixture was stirred.

| | |
|---|---|
| 1. Aluminium chloride hexahydrate | 60.0 g |
| 2. Hydroxypropyl-β-cyclodextrin | 5.0 g |
| 3. Glycerol | 20.0 g |
| 4. Propylene glycol | 20.0 g |
| 5. 70% ethanol preparation | 9.0 g |
| 6. 10% sodium hydroxide | 150.0 g |

In the present Example, in order to reduce irritating nature at affected areas due to the acidity of aluminium chloride, the solution was neutralised with sodium hydroxide and adjusted to pH 3.5, and the precipitate was removed by filtration.

<Case Study 6 of Example 3>

Use example to skin defecting injury after debridement of skin necrosis due to infectious atheroma in the left femoral region: A 60-year-old male.

The patient was aware of an asymptomatic, elastic and soft skin mass with a diameter of 1 to 2 cm on the front side of the left distal femoral region without attention since around March 2014. The mass gradually grew and the patient made the first visit on 26 Sep. 2014 with unbearable pain. Previous medical history: alcoholic cirrhosis (+), the patient orally takes ursodeoxycholic acid, proheparum-containing tablets, portolac powder, Livact-containing granules, spironolactone tablets, Nexium capsules and Vitamedin-containing capsules. At the first visit, an infectious atheroma having a diameter of 6 cm and skin necrosis at ¾ on the rostral side were observed. Therefore, under a local anaesthesia using lidocaine containing 1% epinephrine, dead skin was removed by debridement, the content of atheroma was removed and the wound was cleaned. FIG. 11 to FIG. 17 show the images over time since immediately after the treatment with the formulation of [Example 3] after incision of infectious atheroma with skin necrosis and cleaning of the wound.

The time-dependent change of the case is shown.

2 October (7 days after treatment) (FIG. 11)
Adhesion of fibrin and clot, ulceration.
6 October (11 days after treatment) (FIG. 12)
Observation of hyperplasia of granulation tissue, erosive inflammation at the wedge of the wound.
9 October (14 days after treatment) (FIG. 13) Stabilisation of granulation tissue, epidermalisation at the edge of the wound.
14 October (20 days after treatment) (FIG. 14)
Hyperplasia of benign granulation tissue, initiation of epidermalisation
18 October (24 days after treatment) (FIG. 15)
Completion of ¼ of epidermalisation
27 October (36 days after treatment) (FIG. 16)
Completion of ¾ of epidermalisation, observation of reduction of scar in the vertical direction
30 October (39 days after treatment) (FIG. 17)
Completion of 100% of epidermalisation, observation of pink colour which indicates the progress towards maturation and of reduction of the whole scar. No formation of hypertrophic scar is observed.

EXAMPLE 4

Relative to 100 g of base powder, 10 g of aluminium chloride hexahydrate and 10 g of β-CD were introduced in a ceramic ball mill and ground for 30 minutes to obtain a powder antipruritic agent which was a ground mixture passing through a 48-mesh screen. The base powder was prepared by mixing 5 g of silica, 35 g of zinc flower, 40 g of talc and 20 g of corn starch.

EXAMPLE 5

Relative to 100 g of base powder, 10 g of aluminium hydroxychloride and 10 g of α-CD were introduced in a ceramic ball mill and ground for around 25 minutes to obtain a powder antipruritic agent which was a ground mixture passing through a 48-mesh screen. The base powder was prepared by mixing 5 g of silica, 35 g of zinc flower, 40 g of talc and 20 g of corn starch.

<Case of Example 5>

Figure 18:
FIG. 18 is a photographic image showing the status when first visit with the formulation of Example 5.
Figure 19:
FIG. 19 is a photographic image showing the status 2 months after treatment with the formulation of Example 5.
Figure 20:
FIG. 20 is a photographic image showing the status when first visit with the formulation of Example 6.

A 26-year-old man who visited on 1 Nov. 2014 and wanted to remove nevus pigmentosus on his back by using a carbon dioxide gas laser. At the first visit, the raised nevus pigmentosus of 6 mm could be seen below the left scapula. Under the local anesthesia, vaporization treatment was carried out by using a carbon dioxide gas laser manufactured by HOYA in super pulse mode (S-2) (FIG. 18). From the same day, the patient started to use the agent of the present invention. The agent was applied to the affected site once daily after taking a bath with a protection of gauze. On 29 December, which was after 2 month from the first visit, the patient visited again (FIG. 19). The affected site was cured forming circular pockmark that was not noticeable. The patient was quite satisfied. In the treatment of the carbon dioxide gas laser, since heat energy is high, wound edge and thermal burn are accompanied. Especially when applied to large lesion like this case, there is high possibility that keloids and recessed scar are formed. However, by using the agent of the present invention, the effect of the treatment was satisfactory for the patient without using antibacterial agents and disinfectants.

EXAMPLE 6

Relative to 100 g of base powder, 7 g of aluminium chloride hexahydrate and 8 g of γ-CD were introduced in a ceramic ball mill and ground for around 15 minutes to obtain a powder antipruritic agent which was a ground mixture passing through a 48-mesh screen. The base powder was prepared by mixing 5 g of silica, 35 g of zinc flower, 35 g of talc and 20 g of corn starch.

<Case of Example 6>

Figure 21:
FIG. 21 is a photographic image showing the status 10 days after treatment with the formulation of Example 6.

A 40 year-old woman On 16 November, boiled water boiled water was poured on her right ankle joint at her house and affected by 2nd degree superficial burn. She used a commercial chemical but she became anxious because oedematous blister was formed. She visited on 17 November. At the first visit, flaccid blister of 30 cm could be seen in a belt-like shape. From the same day, the patient started to use the agent of the present invention. Antibacterial agents and disinfectants were not used. From the third day after the treatment was started, pain was disappeared. On 17 November, which was 10th day from the start of treatment, the patient visited again. The scab was coming off and epidermalization seems to have been almost finished (complete therapy) (FIG. 21).

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A method for coating a skin abrasion, a laceration, a burn or an oedema after surgery, comprising the step of:
    applying a biological film-forming agent comprising an aluminium chloride, a cyclodextrin, an ethanol and a water to a patient in need of treatment of the skin abrasion, the laceration, the burn or the oedema after surgery to form a film by demulsifying emulsion formed by skin stratum corneum, sweat and sebum by the aluminium chloride and encapsulating the demulsified components by the cyclodextrin.

2. The method for coating the skin abrasion, the laceration, the burn or the oedema after surgery according to claim 1, wherein
    the biological film-forming agent is an aqueous solution having pH in a range of 1.8 to 7.

3. The method for coating the skin abrasion, the laceration, the burn or the oedema after surgery according to claim 1, wherein
    a concentration of the aluminium chloride is 7.0 to 12.0% by weight per 100 parts of the water.

4. The method for coating the skin abrasion, the laceration, the burn or the oedema after surgery according to claim 1, wherein
    a concentration of the cyclodextrin is 0.1 to 45% by weight per 100 parts of the water.

5. The method for coating the skin abrasion, the laceration, the burn or the oedema after surgery according to claim 1, wherein
    the biological film-forming agent is porous.

6. The method for coating the skin abrasion, the laceration, the burn or the oedema after surgery according to claim 1, wherein
    the biological film-forming agent coats an organ, a damaged site of the organ, or the wound surface reaching a periosteum or a bone cortex.

7. The method for coating the skin abrasion, the laceration, the burn or the oedema after surgery, wherein
    the water is a water content in a body fluid.

8. The method for coating the skin abrasion, the laceration, the burn or the oedema after surgery according to claim 1, wherein
    a dosage form of the biological film-forming agent is an aqueous solution, and
    pH is raised to at least 2.8 by disacidifying the water solution with an alkaline agent and adding a flocculation agent to filter a generated flocculated precipitate.

9. The method for coating the skin abrasion, the laceration, the burn or the oedema after surgery according to claim 1, wherein
    the film urges defatting property, urges function of blocking protein, and suppress production of fibrin so as to suppress inflammation reaction and immunoreaction.

* * * * *